United States Patent [19]

Zweig et al.

[11] 4,199,510

[45] Apr. 22, 1980

[54] PROCESS FOR OXIDATION OF 4-AMIDOTETRAHYDROBENZO [b]-THIOPHENES TO 7-KETO DERIVATIVES WITH COBALTIC SALTS

[75] Inventors: Arnold Zweig, Westport; Robert G. Fischer, Jr., Fairfield, both of Conn.

[73] Assignee: American Cyanamid Company, Stamford, Conn.

[21] Appl. No.: 893,225

[22] Filed: Apr. 4, 1978

Related U.S. Application Data

[63] Continuation of Ser. No. 774,568, Mar. 4, 1977, abandoned.

[51] Int. Cl.$^2$ .................. C07D 209/34; C07C 45/00; C07D 333/24; C07D 333/16
[52] U.S. Cl. ........................... 260/326 S; 260/326 R; 260/586 P; 549/59; 549/75
[58] Field of Search ............... 260/332.3 P, 586 P, 260/332.2 R, 332.2 A, 326 S, 326 R

[56] References Cited

U.S. PATENT DOCUMENTS

| | | | |
|---|---|---|---|
| 2,223,494 | 12/1940 | Loder | 260/586 P |
| 2,386,372 | 10/1945 | Wagner | 260/586 P |
| 3,317,592 | 5/1967 | MacLean | 260/533 |
| 3,946,079 | 3/1976 | Paasen | 260/586 P |
| 3,994,924 | 11/1976 | Asato | 260/332.3 P |

*Primary Examiner*—Alan Siegel
*Attorney, Agent, or Firm*—Harry H. Kline

[57] ABSTRACT

There is provided a process for the preparation of an amido or an ureido derivative of certain 4,5,6,7-tetrahydro-7-oxobenzo[b]thiophenes or certain 1,2,3,4-tetrahydro-4-oxonaphthalenes which can be employed as an animal growth regulant. The process comprises: oxidizing in the presence of a cobaltic carboxylate reactant and in the absence or presence of air, a compound having the formula:

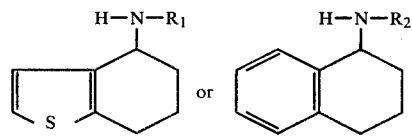

wherein $R_1$ and $R_2$ are each a substituent selected from the group consisting of alkanoyl $C_1$–$C_7$, halogen-substituted alkanoyl $C_1$–$C_7$, carboalkoxy $C_1$–$C_4$,

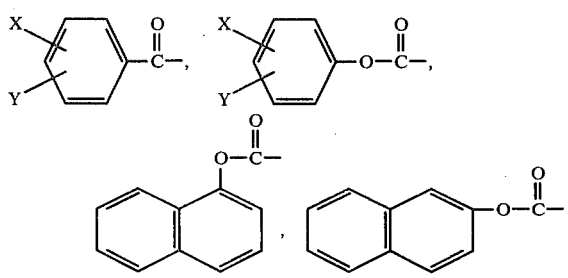

and

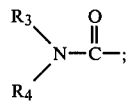

$R_3$ is selected from the group consisting of hydrogen and alkyl $C_1$–$C_4$; $R_4$ is selected from the group consisting of hydrogen, alkyl $C_1$–$C_8$, alkanoyl $C_2$–$C_4$, halogen-substituted alkanoyl ($C_2$–$C_4$), and

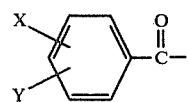

and when the

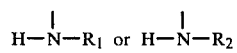

moiety is cyclized each represents a moiety selected from the group consisting of succinimido, maleimido and phthalimido; X and Y are each a radical selected from the group consisting of hydrogen, fluorine, chlorine, bromine, iodine, nitro, alkyl $C_1$–$C_4$; the racemic mixtures and the optical isomers thereof.

4 Claims, No Drawings

PROCESS FOR OXIDATION OF 4-AMIDOTETRAHYDROBENZO [b]-THIOPHENES TO 7-KETO DERIVATIVES WITH COBALTIC SALTS

This application is a continuation of our copending application, Ser. No. 774,568, filed on Mar. 4, 1977, now abandoned.

The present invention relates to a novel process for the preparation of amido and ureido derivatives of 4,5,6,7-tetrahydro-7-oxobenzo[b]thiophene and 1,2,3,4-tetrahydro-4-oxo-naphthalene which are useful as animal growth regulants. More particularly, it relates to the oxidation of amido or ureido derivatives of 4,5,6,7-tetrahydro-benzo[b]thiophenes or 1,2,3,4-tetrahydro-4-oxo-naphthalenes. Still more particularly, it is concerned with a process for the preparation of an amido or an ureido derivative of certain 4,5,6,7-tetrahydro-7-oxobenzo[b]thiophenes or certain 1,2,3,4-tetrahydro-4-oxonaphthalenes which comprises oxidizing in the presence of a cobaltic carboxylate reactant in the absence or presence of air a compound having the formula:

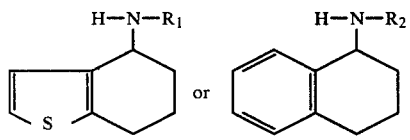

wherein $R_1$ and $R_2$ are each a substituent selected from the group consisting of alkanoyl $C_1$-$C_7$, halogen-substituted alkanoyl $C_1$-$C_7$, carboalkoxy $C_1$-$C_4$,

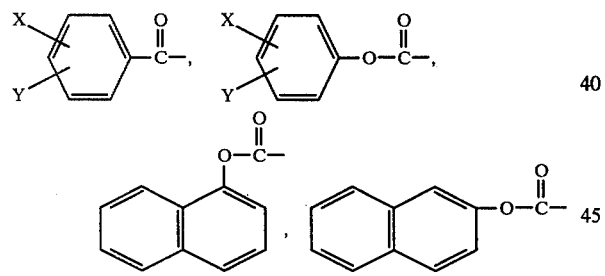

and

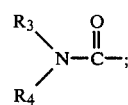

$R_3$ is a radical selected from the group consisting of hydrogen and alkyl $C_1$-$C_4$; $R_4$ is a radical selected from the group consisting of hydrogen, alkyl $C_1$-$C_8$, and alkanoyl ($C_2$-$C_4$), halogen-substituted alkanoyl ($C_2$-$C_4$) and

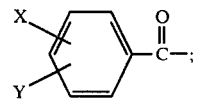

and when the

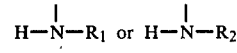

moiety is cyclized, each represents a moiety selected from the group consisting of succinimido, maleimido and phthalimido; X and Y are each a radical selected from the group consisting of hydrogen, fluorine, chlorine, bromine, iodine, nitro, alkyl $C_1$-$C_4$; the racemic mixtures and the optical isomers thereof.

The above-identified tetrahydro-oxobenzo[b]-thienylureas are useful as animal growth promoting agents as disclosed in German Offenlegungschrift No. 2,501,788, published on July 7, 1975. Since there is an ever increasing demand for greater food production, animal growth-promoting agents are of considerable interest. Consequently, it is of prime importance to find processes suitable for large-scale manufacturing of said animal growth-promoting compounds in satisfactory yields.

In accordance with the process of the invention, it has been found that one of the alpha-methylene groups of a cycloalkanoheterocycle of formula (I) or benzocycloalkane of formula (II) set forth hereinbelow can be oxidized, albeit in the presence of a nitrogen containing functional group, such as an amido or ureido group attached to the carbon atom of the second alpha-methylene group, so as to obtain in good yields and purity the corresponding oxo compounds of formula (III) or (IV), respectively, as graphically illustrated:

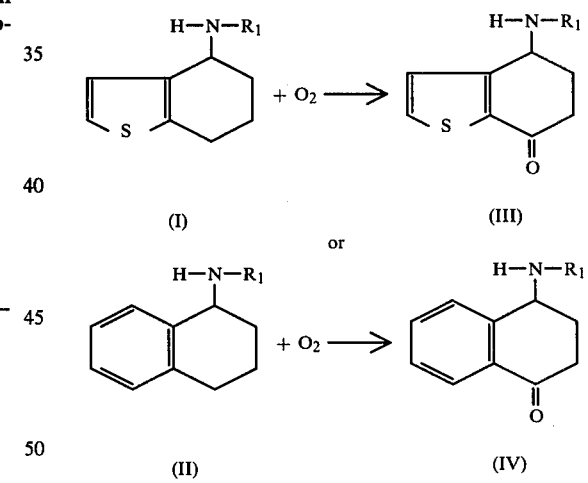

where $R_1$ and $R_2$ are each defined above.

A preferred group of compounds represented by formula (I) or (II) above is that wherein $R_1$ and $R_2$ are each a radical selected from the group consisting of alkanoyl $C_1$-$C_7$, halogen-substituted alkanoyl $C_2$-$C_4$, benzoyl and

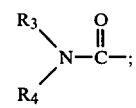

$R_3$ is a radical selected from the group consisting of hydrogen and alkyl $C_1$-$C_4$; $R_4$ is a radical selected from the group consisting of hydrogen, alkyl $C_1$-$C_8$, acetyl, trichloroacetyl and benzoyl; and where the

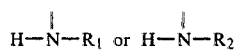

moiety is cyclized, each represents phthalimido; the racemic mixtures and the optical isomers thereof are oxidized in accordance with the process of the invention to the corresponding formula (III) or (IV), above.

Another preferred group of compounds represented by formula (I) or (II) above is that wherein $R_1$ and $R_2$ are each a radical selected from the group consisting of formyl, acetyl,

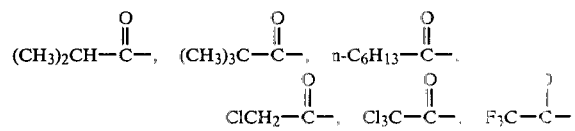

benzoyl and

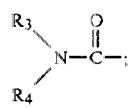

$R_3$ is a radical selected from the group consisting of hydrogen, methyl and iso-propyl; $R_4$ is a radical selected from hydrogen, methyl, n-octyl and benzoyl; and when the

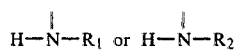

moiety is cyclized, each represents phthalimido; the racemic mixtures and the optical isomers thereof are oxidized by the process of the invention to the corresponding formula (III) or (IV), above.

As hereinabove indicated, the 4,5,6,7-tetrahydro-7-oxobenzo[b]thien-4-ylurea compounds of formula (III) and the 1,2,3,4-tetrahydro-4-oxo-1-naphthylurea compounds of formula (IV) are valuable and useful growth promoting agents for poultry, fur-bearing animals and farm animals.

In general, a compound represented by formula (I) or (II) above is oxidized in the presence of a cobaltic carboxylate reactant such as cobaltic acetate or cobaltic propionate utilizing stoichiometric amounts of the same and in the absence or presence of air in a water solution containing from about 0% to about 90% of an aliphatic monocarboxylic acid, such as acetic and, n-propionic acid, n-butyric acid and equivalents of the same at a temperature ranging from about 20° C. to about 100° C. and, preferably at from 50° C. to 60° C.

The overall reaction can be graphically illustrated as follows:

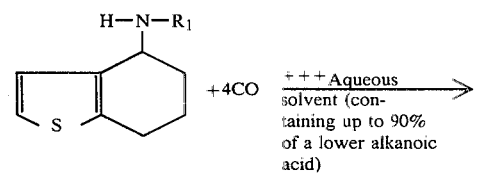

(I)

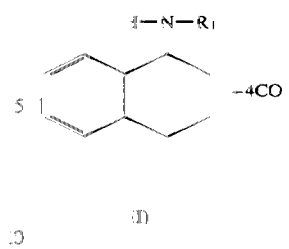

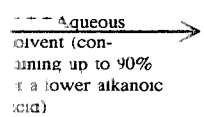

(II)

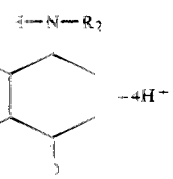

(V)

Thus, when $R_2$ is

and $R_3$ and $R_4$ are as hereinabove defined, the oxo compounds obtained by the above process are usually the desired animal growth promoting ureas, namely, 4,5,6,7-tetrahydro-7-oxobenzo[b]thien-4-ylureas of formula (VII) and 1,2,3,4-tetrahydro-4-oxo-1-naphthylureas of formula (VIII) as graphically illustrated below.

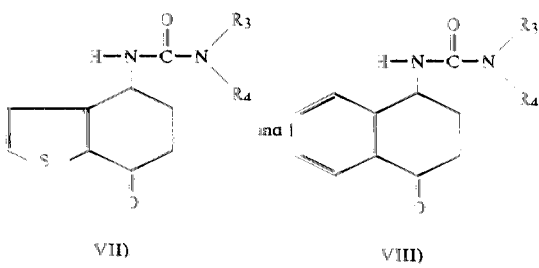

(VII) and (VIII)

wherein $R_3$ is selected from the group consisting of hydrogen, and alkyl $C_1-C_4$; $R_4$ is hydrogen, alkyl $C_1-C_4$, alkanoyl $C_2-C_4$, halogen-substituted alkanoyl $C_2-C_4$ and

X and Y are selected from the group consisting of hydrogen, halogen, nitro and alkoxy $C_1-C_4$; the term "halogen" is used above to represent bromine, chlorine, fluorine and iodine; and said compounds are the racemic mixtures and the optical isomers thereof.

When $R_4$ is defined as alkanoyl ($C_2$-$C_4$), halogen-substituted alkanoyl ($C_2$-$C_4$) or

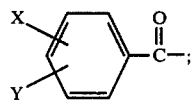

X and Y are as defined above, alkaline hydrolysis of these ureas affords ureas of formulae (VII) and (VIII), wherein $R_4$ is hydrogen.

However, when $R_2$ is not

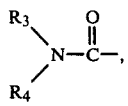

then the oxo compounds obtained by the above process are the corresponding formulae (III) and (IV) amides and imides, where

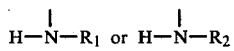

is each cyclized to form a moiety selected from the group of cyclic imides consisting of succinimido, maleimido and phthalimido. These amides and imides can be converted in a straightforward manner to the desired formula (VII) or (VIII) urea compound as follows: As amide (or imide) of formula (III) or formula (IV) is hydrolyzed with dilute acid or alkali, preferably an acid, e.g. hydrochloric acid to the corresponding formula (V) or formula (VI) amine (or a salt thereof) as hereinbelow graphically illustrated:

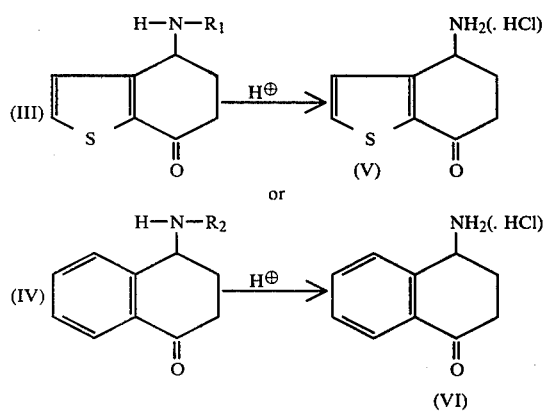

wherein $R_1$ and $R_2$ are each a radical selected from the group consisting of alkanoyl $C_1$-$C_6$, halogen-substituted alkanoyl ($C_1$-$C_6$), carboalkoxy ($C_1$-$C_4$)

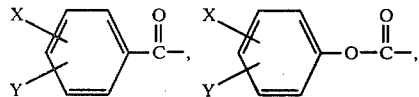

-continued

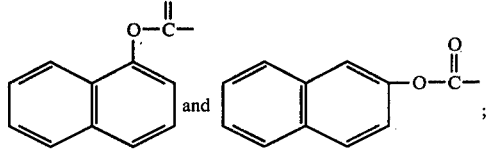

and when

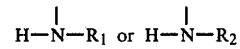

is each cyclized, each represents a moiety selected from the group consisting of succinimido, maleimido and phthalimido; X and Y are selected from the group consisting of hydrogen, halogn, nitro and alkoxy $C_1$-$C_4$; said "halogen" denoting bromide, chlorine, fluorine and iodine and said compounds are the racemic mixtures and the optical isomers thereof.

Formula (VII) above, namely 4,5,6,7-tetrahydro-7-oxobenzo[b]thien-4-ylurea compounds and formula (VIII) above, namely, 1,2,3,4-tetrahydro-4-oxo-1-naphthylurea compounds, wherein $R_3$ and $R_4$ are hydrogen can be advantageously prepared from the above-identified formula (V) or (VI) amines or acid salts thereof, by reacting said amines with an approximately equimolar amounts of sodium or potassium cyanate. However, it is generally preferable to employ from about 5% to about 50% excess of a suitable cyanate. The reaction can be conducted at atmospheric or superatmospheric pressure at a temperature in the range of 0° C. to 100° C., but is preferably conducted at atmospheric pressure at 0° C. to 70° C. in the presence of a solvent, such as water, $C_1$-$C_3$ aliphatic alcohol, tetrahydrofuran, dioxane, ethylene glycol dimethyl ether, acetone, methyl ethyl ketone, and mixtures thereof in the pH range of from 5 to 7 and, preferably, at pH 6. The above reaction may be graphically illustrated as follows:

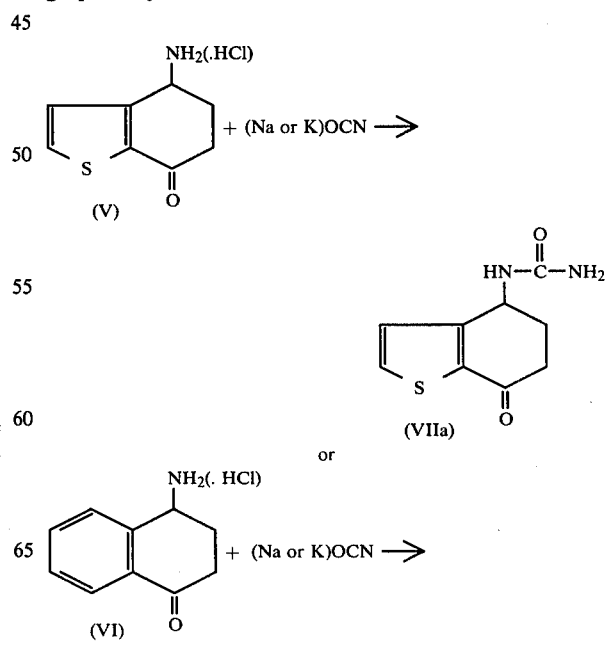

-continued

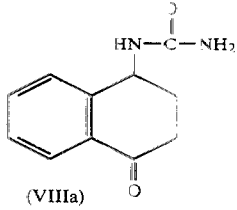
(VIIIa)

Substituted ureas of formula (VII) or (VIII) can be prepared advantageously by treating the above-identified amines of formulae (V) or (VI) with an appropriately substituted alkyl isocyanate of formula: $R_3$—NCO or with a carbamoyl halide of the formula

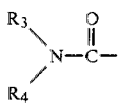

halide, wherein $R_3$ and $R_4$ are alkyl as hereinabove defined and the halide is chloro or bromo. The free bases of formula (V) or (VI) or the acid addition salts thereof, preferably the hydrochloride, can be employed in the presence of an acid acceptor. Illustrative acid acceptors are pyridine, triethylamine or any suitable tertiary amine, alkali metal carbonates, such as potassium carbonate and sodium carbonate, strong basic ionexchange resins, and aqueous alkali. The reaction may be run from about 0° C. to 100° C. and, preferably, at 0° C. to 70° C. until the desired reaction is complete. The isocyanate or carbamoyl halide is generally employed in equimolar amounts, but it may be used in excess.

As stated above, formulae (VII) and (VIII) compounds are useful as growth promoting agents for animals, such as poultry, fur-bearing and farm animals, and the use of said compounds for this purpose provides the added advantage of improving feed conversion for said animals. The term "feed conversion" means the ratio of unit weight of feed per unit weight of gain and the improvement in feed conversion means increased weight gain from a given unit of feed consumed.

A growth-promoting amount of a formula (VII) or a formula (VIII) compound or an optically active isomer thereof is administered to a host animal in, or with, the animal's feed. Said compound may also be administered as a subcutaneous implant under the skin of said animal or as a parenteral injection. When administered in the feed of said animals, usually from about 0.0001% to about 0.08% by weight, and, preferably, from 0.001% to 0.04% by weight of formula (VII) or formula (VIII) urea, is effective for increasing growth rate and improving feed conversion. When administered as a parenteral injection or subcutaneous implant, usually in amounts that will supply about 0.0005 mg to about 0.2 mg, preferably 0.001 mg to 0.1 mg per kg of body weight per day of the active compound, it will produce the desired improvement in weight gain and will enhance feed conversion.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE I

Preparation of Cobaltic Acetate

An aqueous solution of cobaltous acetate (140 ml) saturated at 0° C. (0.29 g/ml) is placed in a 500 ml Erlenmeyer flask. The solution is cooled in an ice bath to 4° C. Addition of 23 ml of 40% peracetic acid is made in small portions (over about 15 minutes) with shaking. This and subsequent additions are made at a rate such that the temperature remains between 4.0° and 5° C. About 4 minutes after the peracetic acid addition is completed, 9 g of powdered $Co(OAc)_2 \cdot 4H_2O$ are added to the reaction mixture in portions over 2 minutes. This is followed after one minute by a further addition of 5 ml of peracetic acid. The cycle of addition of 9 g powdered $Co(OAc)_2 \cdot 4H_2O$ and 5 ml peracetic acid portions is repeated five more times and then concluded with a final addition of 9 g of $Co(OAc)_2 \cdot 4H_2O$. The total reaction time is about 1.5 hours.

Resultant final dark green solution is filtered to yield a solution volume of 228 ml. Iodometric titration of one ml of this solution indicated 0.002 mole of $Co^{3+}$/ml.

EXAMPLE II

Preparation of Cobaltic Acetate by Co-oxidation of $Co(OAc)_2$ and Acetaldehyde with Oxygen In a cylindrical tube with a fritted bottom is placed 40 ml of glacial acetic acid and the temperature is adjusted to 60° C. A mixture of oxygen and acetaldehyde formed by passing oxygen through liquid acetaldehyde at $-5°$ C.) is passed through the fritted bottom into the acetic acid at about 400 ml/min. 25.0 g of $Co(OAc)_2 \cdot 4H_2O$ is then added. About ½ hour after the addition is completed, the reaction becomes exothermic. The temperature is then kept at 80° C. by adjusting the oxygen flow rate. One hour after the exotherm occurred, the reaction is terminated. This gave 58 ml of a solution, 1.43 M in Co(III) (82.7% conversion), as determined by iodometric titration.

The corresponding cobaltic propionate can be prepared by replacing acetic acid with propionic acid, acetaldehyde with propionaldehyde and cobaltous carbonate in lieu of cobaltous acetate in the above procedure.

EXAMPLE III

This example illustrates the Isolation of Solid Cobaltic Acetate From Its Solution Solid cobaltic acetate is prepared by high vacuum evaporation of the cobaltic acetate solution of Example I. Thus, the solution in Example II was evaporated at 25° C. and 0.4 mm Hg. for 36 hours to give 21.45 g. of a black solid which analyzed as 22.79% Co(III), by weight as determined by iodometric titration.

Example IV

Preparation of Sodium Tricarbonate cobaltate Trihydrate

There is slurried, 42 g. of sodium bicarbonate and 50 ml of $H_2O$ in an ice bath. To this solution is added a mixture of 29.1 g. of $Co(NO_3)_2 \cdot 6H_2O$ and 10 ml of 30% $H_2O_2$ in 50 ml of cold $H_2O$. Resultant product is then stirred for one hour, filtered, washed successively with cold $H_2O$, ethanol, and ether and air dried. An olive green powder, 28.1 g (78%) containing 11.7% Co(III) by weight is obtained.

EXAMPLE V

Preparation of N-(4,5,6,7-tetrahydro-7-oxobenzo[b]thien-4-yl)acetamide

Into a suitable 500 ml flask fitted with a thermometer, mechanical stirrer, and condenser are placed 15.0 g of N-(4,5,6,7-tetrahydrobenzo[b]thien-4-yl)acetamide, 100 ml of acetic acid and 210 ml of the $Co^{3+}$ solution as prepared in Example 1 above. The solution is heated to 59°–61° and stirred at this temperature for about 14 hours. The reaction mixture is cooled, seeded with a few crystals of $Co(OAc)_2.4H_2O$ and stirred for ½ hour. The mixture is then filtered. Addition of ethyl acetate (600 ml) and stirring produces a further quantity of precipitate, removed by filtration.

The filtrate solution is extracted with 100 ml of water to give a very dark aqueous solution and an orange-brown ethyl acetate solution. The latter is concentrated in a rotating evaporator to yield a brown oil. This oil is treated with 50 ml of chloroform and 50 ml of water and the mixture shaken. The resulting layers are separated. The chloroform extract is dried with sodium sulfate and the chloroform is removed leaving an orange oil that slowly solidified. The solid is thoroughly dried in vacuo to yield 15.22 g of light tan product. High pressure liquid chromatography analysis of this solid indicated 74.5% by weight of the title Compound.

EXAMPLE VI

Preparation of 4,5,6,7-tetrahydro-7-oxobenzo[b]thien-4-ylurea

The product from Example V is stirred in a mixture of 75 ml water and 75 ml concentrated hydrochloric acid and heated at reflux for 4 hours. The reaction mixture is cooled, the solution decanted from the brown semi-solid, which is then further washed with water. The combined aqueous solutions are evaporated to afford brown crystals.

The above crystals are dissolved in 75 ml water and a solution of 19.1 g potassium cyanate in 50 ml water is added and the reaction mixture stirred overnight. The reaction mixture is then filtered, the solid collected is washed successively with 500 ml water and 50 ml of cold methanol to attain yield of 83% of the title compound, having a melting point of 234° C. to 236° C.

EXAMPLE VII

Preparation of N-(4,5,6,7-tetrahydro-7-oxo-benz[b]-thien-4-yl)acetamide Using the Oxidant of Example II Into a 100 ml, three necked round bottomed flask is placed 2.0 g of N-(4,5,6,7-tetrahydrobenz[b]-thien-4-yl)acetamide, 15 ml of $H_2O$, and 31.5 ml of a 1.3 M cobaltic acetate solution prepared as in Example II. The mixture is stirred and heated to 60° C. under $N_2$ for 12 hours and is worked up as in Example V. A material weighing 1.9 g and assaying as 76.8% of the product was obtained.

EXAMPLE VIII

Preparation of N-(4,5,6,7-tetrahydro-7-oxo-benz[b]-thien-4-yl)acetamide Using the Oxidant of Example III In a 100 ml three-necked round bottomed flask is placed 1.0 g. of N-(4,5,6,7-tetrahydrobenz[b] thien-4-yl)acetamide, 5 ml each of $H_2O$ and glacial acetic acid, and 5.13 g. of solid cobaltic acetate (assay 23.56% Co(III) by weight) prepared by method of Example V). The mixture is stirred and heated to 60° C. for 11 hours under a nitrogen atmosphere. Treatment as in Example V yields 1.04 g. of material containing 79.6% of the desired product.

EXAMPLE IX

Preparation of N-(4,5,6,7-tetrahydro-7-oxo-benz[b]-thien-4-yl) acetamide Using the Oxidant of Example IV Into a 100 ml three-necked round bottomed flask is placed 0.5 g. of N-(4,5,6,7-tetrahydrobenz[b]-thien-4-yl) acetamide and 6.85 g. of sodium triscarbonatocobaltate (essay 8.86% Co(III)) and 25 ml of $H_2O$. 30 ml of acetic acid is added, dropwise at first and then more rapidly as carbon-dioxide evolution diminished. The solution is stirred and heated to 60° C. for 5 hours and is worked up as in Example V to yield 0.42 g of material assaying 94%, by weight, of the title compound.

EXAMPLE X

Preparation of 4,5,6,7-tetrahydro-7-oxobenzo[b]-thien-4-ylurea from 4,5,6,7-tetrahydro-benzo[b]-thien-4-ylurea In a 100 ml flask is placed 2.0 g of 4,5,6,7-tetrahydrobenzo[b] thien-4-ylurea, 10.6 g. of solid cobaltic acetate prepared by the method of Example VI, and 35 ml of water. The mixture is stirred and heated at 62° C. for 12 hours. The solution is cooled to room temperature and filtered. The solid product is washed with water until the washing is clear and allowed to air dry. Analysis indicated the presence of 1.39 g. (65%) of the desired product.

EXAMPLE XI

Preparation of 4,5,6,7-tetrahydro-7-oxobenzo[b]-thien-4-ylurea

The reaction described in Example VII is repeated in all details except that the solvent consisted of 17.5 ml of water and 17.5 ml of acetic acid. Analysis indicated 1.28 g. (50%) of the desired product and 0.05 g. of unreacted starting material.

EXAMPLE XII

Preparation of N-(1,2,3,4-tetrahydro-4-oxo-1-naphtyl)acetamide

Following the procedure of Example V except that N-(1,2,3,4-tetrahydro-1-naphthyl)acetamide is employed in lieu of N-4,5,6,7-tetrahydrobenzo[b]thien-4-yl acetamide there is recovered the title compound in a yield of 76%.

We claim:

1. A process for the preparation of a compound of the formula:

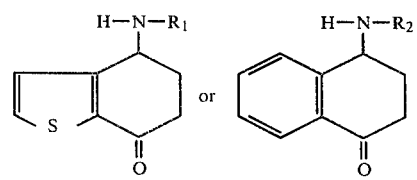

wherein $R_1$ and $R_2$ are each a substituent selected from the group consisting of alkanoyl $C_1$–$C_7$, halogen-substituted alkanoyl $C_1$–$C_7$, carboalkoxy $C_1$–$C_4$,

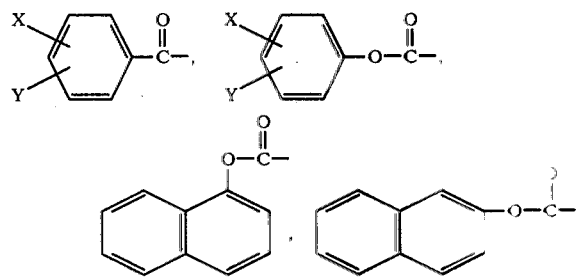

and

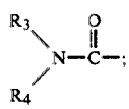

$R_3$ is a radical selected from the group consisting of hydrogen and alkyl $C_1$–$C_4$; $R_4$ is a substituent selected from the group consisting of hydrogen, alkyl $C_1$–$C_8$, alkanoyl ($C_2$–$C_4$), halogen-substituted alkanoyl ($C_2$–$C_4$) and

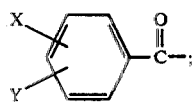

when the $$H-N-R_1 \text{ or } H-N-R_2$$

moiety is cyclized, each represents a moiety selected from the group consisting of succinimido, maleimido and phthalimido; X and Y are each a radical selected from the group consisting of hydrogen, fluorine, chlorine, bromine, iodine, nitro, alkyl $C_1$–$C_4$; consisting essentially in the step of reacting a compound of the formula:

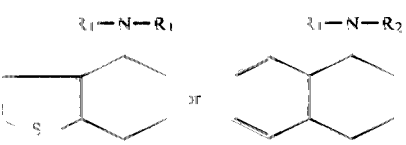

wherein $R_1$ and $R_2$ are as hereinabove defined; with a cobaltic carboxylate reactant in stoichiometric quantities at temperatures ranging from 20° C.–100° C.

2. The process according to claim 1 wherein the compound to be oxidized is selected from the formula consisting of:

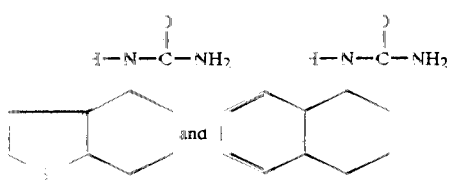

3. The process according to claim 1 wherein the cobaltic carboxylate reactant is cobaltic acetate.

4. The process according to claim 1, wherein the cobaltic carboxylate reactant is cobaltic propionate.

* * * * *